US00PP28050P3

(12) United States Plant Patent
Vanderhaegen

(10) Patent No.: US PP28,050 P3
(45) Date of Patent: May 23, 2017

(54) ***RHODODENDRON* PLANT NAMED 'HORT12'**

(50) Latin Name: *Rhododendron simsii*
Varietal Denomination: HORT12

(71) Applicant: Johan Vanderhaegen, Kruishoutem (BE)

(72) Inventor: Johan Vanderhaegen, Kruishoutem (BE)

(73) Assignee: Hortibreed NV, Lochristi (BE)

( * ) Notice: Subject to any disclaimer, the term of this patent is extended or adjusted under 35 U.S.C. 154(b) by 0 days.

(21) Appl. No.: 14/999,053

(22) Filed: Mar. 23, 2016

(65) Prior Publication Data

US 2016/0309635 P1 Oct. 20, 2016

(30) Foreign Application Priority Data

Apr. 14, 2015 (QZ) ..... PBR 2015/0838

(51) Int. Cl.
*A01H 5/00* (2006.01)

(52) U.S. Cl.
USPC ..... Plt./238

(58) Field of Classification Search
USPC ..... Plt./238
See application file for complete search history.

*Primary Examiner* — Annette Para

(57) ABSTRACT

A new cultivar of *Rhododendron* plant named 'HORT12' that is characterized by shiny green leaves, white double flowers with a green throat and a long flowering time.

1 Drawing Sheet

Botanical classification: *Rhododendron simsii.*
Variety denomination: 'HORT12'.

BACKGROUND OF THE INVENTION

The present invention relates to a new and distinct cultivar of *Rhododendron* plant botanically known as *Rhododendron simsii* and hereinafter referred to by the cultivar name 'HORT12'.

'HORT12' was discovered as a naturally occurring branch mutation of *Rhododendron simsii* 'Classic Rouge' (U.S. Plant Pat. No. 16,338). 'HORT12' was discovered in February of 2010 in a greenhouse environment in a cultivated area of Moerbeke, Belgium.

Asexual reproduction of the new cultivar 'HORT12' by cuttings was first performed in July of 2010 in Moerbeke, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Rhododendron* cultivar 'HORT12'. These traits in combination distinguish 'HORT12' as a new and distinct cultivar.

1. *Rhododendron* 'HORT 12' exhibits white double flowers with a green throat.
2. *Rhododendron* 'HORT12' exhibits a long flowering time.
3. *Rhododendron* 'HORT12' exhibits shiny green leaves.

The closest comparison variety is the parent plant *Rhododendron* 'Classic Rouge'.

'HORT12' is different than 'Classic Rouge' in having white double flowers with a green throat. In contrast, the flowers of 'Classic Rouge' are red-purple in color.

BRIEF DESCRIPTION OF THE DRAWING

The accompanying photograph illustrates the distinguishing traits of *Rhododendron* 'HORT12'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rhododendron* cultivar named 'HORT12'. Data was collected in Moerbeke, Belgium from 24 month old greenhouse grown plants in 1.0 liter containers. The time of year was Spring and the average temperature was 22° Centigrade during the day and 18° Centigrade at night. The light level was 5000 Klux and there were no photoperiodic treatments. Color determinations are in accordance with The Royal Horticultural Society Colour Chart 2001 edition, except where general color terms of ordinary dictionary significance are used. The growing requirements are similar to the species. 'HORT12' has not been tested under all possible conditions and phenotypic differences may be observed with variations in environmental, climatic, and cultural conditions, however, without any variance in genotype.

Botanical classification: *Rhododendron simsii* 'HORT12'.
Use: Ornamental perennial shrub.
Parentage: 'HORT12' is a naturally occurring branch mutation of *Rhododendron* 'Classic Rouge'.
Vigor: Low to moderate.
Growth rate: Approximately 4.7 cm. per year.
Growth habit: Broad upright, densely branched.
Plant shape: Flattened globose.
Suitable container size: 1.0 liter container.
Height: Average 18 cm. in height.

Width: Average 36 cm. in width.
Hardiness: USDA Zone 9.
Propagation: Cuttings.
Time to initiate roots: Approximately 30 days to produce roots on an initial cutting.
Time to produce a rooted cutting or liner: Approximately 60 days.
Root system: Fine and fibrous.
Stem:
*Branching habit*.—Freely branching.
*Average number of lateral branches*.—4.
*Pinching*.—Yes.
*Lateral branch diameter*.—2.5 mm. in diameter.
*Lateral branch length*.—9.3 cm. in length.
*Lateral branch strength*.—Moderately strong.
*Stem color*.—144A to 144B, older stems 200C to 200D.
*Pubescence*.—Strong, length 1 mm., color 174B.
*Internode length*.—6.7 mm. between nodes.
*Shape*.—Round.
*Surface*.—Dull.
*Stem strength*.—Moderately strong.
Foliage:
*Texture* (*both surfaces*).—Glossy, slightly leathery.
*Leaf arrangement*.—Alternate, clustered towards the top of the stems.
*Compound or single*.—Single.
*Quantity of leaves per lateral branch*.—14.
*Leaf shape*.—Elliptic to obovate.
*Leaf apex*.—Rounded.
*Leaf base*.—Attenuate.
*Leaf length*.—3.5 cm. in length.
*Leaf width*.—1.9 cm. in width.
*Pubescence*.—Slight on both sides, length 1 mm. color 165B to 165C.
*Leaf margin*.—Entire.
*Vein pattern*.—Arcuate.
*Young leaf color* (*upper surface*).—144A.
*Young leaf color* (*lower surface*).—146C.
*Mature leaf color* (*upper surface*).—139A.
*Mature leaf color* (*lower surface*).—137C.
*Vein color* (*lower surface*).—144C.
*Vein color* (*upper surface*).—143B.
*Leaf attachment*.—Petiolate.
*Petiole dimensions*.—5 mm. in length, slightly flattened 2.5 mm. in width, 1 mm. in height.
*Petiole color*.—144C.
*Durability of foliage to stress*.—High.
Flower:
*Flower arrangement*.—Terminal clusters.
*Inflorescence type*.—Umbel.
*Inflorescence dimensions*.—Approx. 7.5 cm. in diameter and 3.6 cm. in height.
*Flowering habit*.—Continuously, once a year.
*Flower form*.—Semi-double, Hose-in-hose.
*Quantity of flowers per lateral stem*.—Approximately 5.
*Quantity of flower buds per lateral stem*.—Approximately 1 to 4.
*Quantity of flowers and buds per plant*.—Approximately 125.
*Flowering season*.—Late winter to early spring.
*Time to flower or response time*.—Flowering 8 months after final pinching.
*Rate of flower opening*.—After the first flower of a cluster has opened, all flowers of that cluster will open in approximately 14 days.
*Fragrance*.—None.
*Self-cleaning or persistent*.—Persistent.
*Flower bud length*.—15 mm. in length.
*Flower bud diameter*.—8 mm. in diameter.
*Flower bud shape*.—Ovate.
*Bud color*.—145A to 145B.
*Rate of bud opening*.—85% in 14 days.
*Flower aspect*.—Upright to outward.
*Flower shape*.—Funnelform.
*Flower dimensions*.—6.5 cm. in diameter and 3.6 cm. in height.
*Flower longevity*.—Lasts approximately 42 days on plant.
*Petal appearance*.—Dull, slightly velvety.
*Petal texture* (*both surfaces*).—Glabrous.
*Petal arrangement*.—Funnelfrom, petals placed rotate.
*Number of petals*.—Five in number.
*Petals fused or unfused*.—Lower 25% fused.
*Petal shape*.—Obovate.
*Petal margin*.—Entire, wavy.
*Petal apex*.—Rounded to praemorse.
*Petal dimensions*.—Approx. 3.7 cm. in length and 2.5 cm. in width.
*Petal color when opening* (*upper side*).—157A.
*Petal color when opening* (*under side*).—157A.
*Petal color when fully opened* (*upper side*).—155C.
*Petal color when fully opened* (*under side*).—155C.
*Petal color fading to*.—Not fading.
*Petaloid appearance*.—Dull, slightly velvety.
*Petaloid arrangement*.—Rotate in the center of the flower.
*Petaloid number*.—Five in number.
*Petaloid shape*.—Irregular, obovate to flabellate.
*Petaloid margin*.—Entire.
*Petaloid dimensions*.—3.0 cm. in length and 1.3 cm. in width.
*Petaloid color immature*.—157A.
*Petaloid color mature*.—155C.
Calyx:
*Calyx shape*.—Funnelform.
*Calyx dimensions*.—5.9 cm. in diameter and 3.6 mm. in width.
Sepals:
*Sepal appearance* (*both surfaces*).—Slightly pubescent.
*Sepal arrangement*.—Rosette.
*Number of sepals*.—Five in number.
*Sepals fused or unfused*.—Fused.
*Sepal shape*.—Irregular, incised.
*Sepal margin*.—Entire, wavy.
*Sepal apex*.—Praemorse.
*Sepal base*.—Spatulate.
*Sepal dimensions*.—1.5 to 3 cm. in length and 1 to 1.5 cm. in width.
*Sepal color when opening* (*upper side*).—157A.
*Sepal color when opening* (*under side*).—157A.
*Sepal color mature* (*upper side*).—155C.
*Sepal color mature* (*under side*).—155C.
Bracts:
*Number of bracts*.—Approx. 6 in number.
*Bract dimensions*.—11 mm. in length and 10 mm. in width.

*Bract shape*.—Rounded.

*Bract apex*.—Rounded.

*Bract pubescence*.—Dense on under side, length 1.0 mm., color, 167C, upper side glabrous.

*Bract color* (*both sides*).—144C (base), 143A (apex).

Pedicels:

*Pedicel dimensions*.—5 mm. in length and 2 mm. in diameter.

*Pedicel angle*.—75°.

*Pedicel color*.—145B.

*Pedicel pubescence*.—Strong, length 0.5 mm., color 192D.

*Pedicel strength*.—Moderate to strong.

Reproduction organs:

*Stamen number*.—Variable, between 0 and 5 in number.

*Anther shape*.—Dorsifixed, oval.

*Anther dimensions*.—1 mm.

*Anther color*.—167C.

*Filament length*.—1.8 cm.

*Filament color*.—155C.

*Amount of pollen*.—Very low.

*Pistil number*.—1 in number.

*Pistil dimensions*.—2.5 cm. in length.

*Stigma shape*.—Club shaped, flattened at the top.

*Stigma color*.—149A.

*Style length*.—2.0 cm.

*Style color*.—157D.

*Ovary color*.—143A.

Fruit and seed: Fruit and seed production has not been observed to date.

Disease and pest resistance: Plants of the new *Rhododendron* have not been observed for disease or pest resistance to date.

The invention claimed is:

1. A new and distinct variety of *Rhododendron* plant named 'HORT12' as described and illustrated.

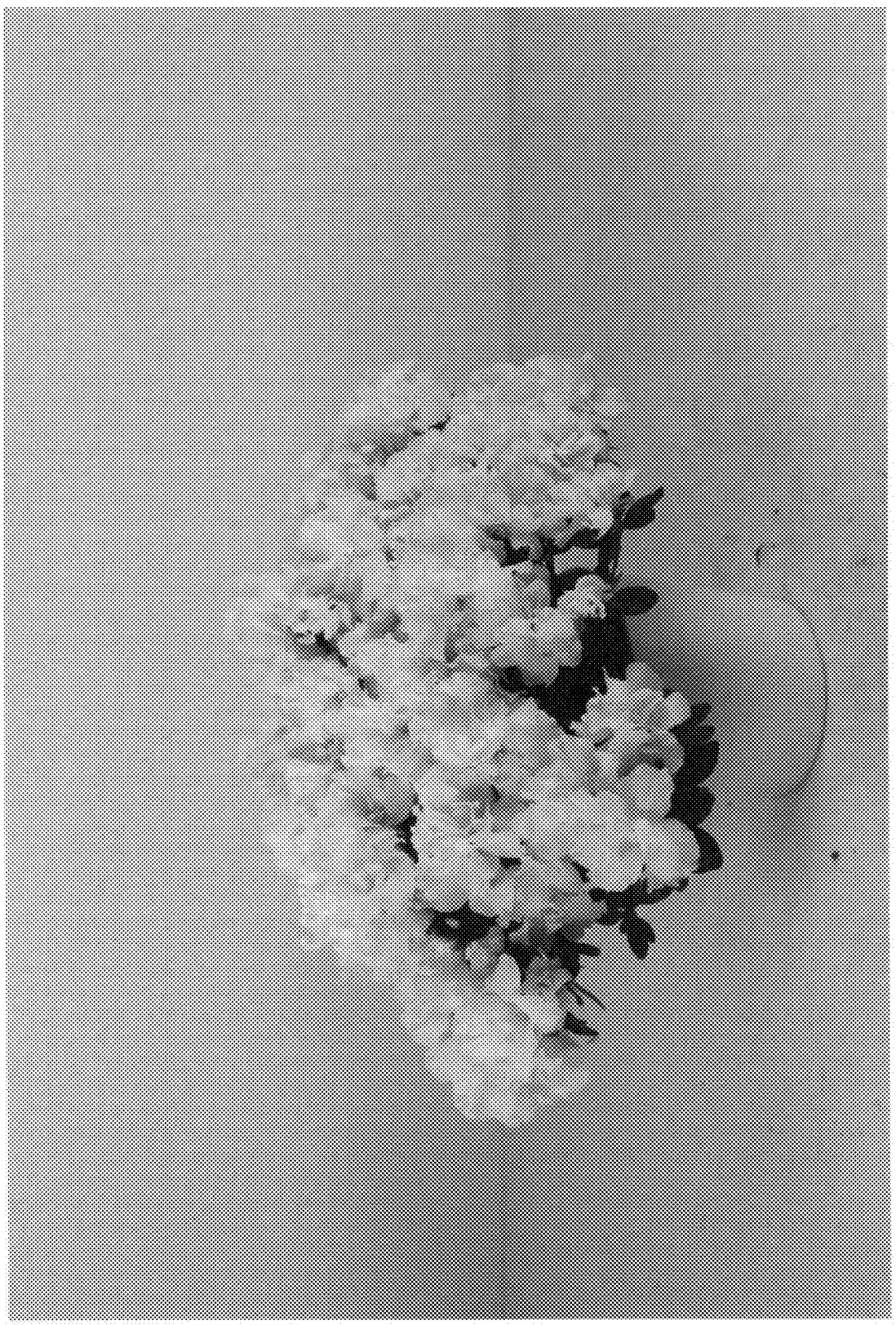

* * * * *